(12) United States Patent
Noeding et al.

(10) Patent No.: US 6,693,131 B2
(45) Date of Patent: Feb. 17, 2004

(54) DELTAMETHRIN-CONTAINING WATER-DISPERSIBLE GRANULES

(75) Inventors: Gunnar Noeding, Morschen-Konnefeld (DE); Agnes Nied, Frankfurt (DE); Andrew Adams, Kriftel (DE); Heiko Diehlmann, Limburg (DE); Manfred Wagenbach, Nidderau-Holdenbergen (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/962,184

(22) Filed: Sep. 24, 2001

(65) Prior Publication Data

US 2003/0099681 A1 May 29, 2003

(30) Foreign Application Priority Data

Sep. 26, 2000 (DE) .......................................... 100 48 006

(51) Int. Cl.⁷ .......................... A01N 53/08; A01N 53/06
(52) U.S. Cl. ....................... 514/521; 514/951; 514/952; 424/489
(58) Field of Search ................................. 514/521, 951, 514/952; 424/489

(56) References Cited

U.S. PATENT DOCUMENTS

| 5,087,456 A | | 2/1992 | Meinard et al. ............. 424/501 |
|---|---|---|---|
| 5,372,989 A | | 12/1994 | Geigle et al. ................ 504/116 |
| 5,705,193 A | | 1/1998 | Bourgogne et al. ......... 424/489 |
| 6,001,382 A | * | 12/1999 | Levy ........................... 424/405 |

FOREIGN PATENT DOCUMENTS

| CA | 1282608 | 4/1991 |
|---|---|---|
| EP | 0 659 341 | 6/1995 |
| FR | 2 713 045 | 6/1995 |
| FR | 2 734 124 | 11/1996 |

\* cited by examiner

*Primary Examiner*—John Pak
(74) *Attorney, Agent, or Firm*—Frommer Lawrence & Haug LLP

(57) ABSTRACT

The invention relates to the formulation of deltamethrin as water-dispersible granules which comprise wetting agents, dispersants, solid inert substances and one or more acids in an amount sufficient to adjust the pH of the mixture to a value in the range from 1 to 7. The granules are particularly useful for controlling animal pests.

3 Claims, No Drawings

DELTAMETHRIN-CONTAINING WATER-DISPERSIBLE GRANULES

The invention relates to formulations of deltamethrin as water-dispersible granules, to a process for their preparation and to the use of such formulations for controlling pests.

Deltamethrin (S-α-cyano-3-phenoxybenzyl-(1R,3R)-3-(2,2-dibromovinyl)-2,2-dimethylcyclopropanecarboxylic acid ester) is an insecticide from the class of the pyrethroids and has been used extensively and for a long time for controlling pests (C. D. S. Tomlin, The Pesticide Manual, 11th Edition, British Crop Protection Council, Farnham 1997).

Numerous formulations have been disclosed, including suspension concentrates, which have the advantage that they do not require any organic solvents. Other solvent-free formulations are water-dispersible granules (WDG) which, when added to water, give a suspension of the deltamethrin particles in water, similarly to suspension concentrates.

EP-A 0 224 845 describes, in a general manner, water-dispersible granules for use in crop protection. A relatively large number of possible active compounds is listed, including deltamethrin. However, an example of a deltamethrin-containing formulation is not given.

Surprisingly, it has now been found that certain WDG formulations of deltamethrin have, on application, considerably better activity than the suspension concentrates which are usually used.

The present invention provides water-dispersible granules, comprising
 a) from 5 to 60% by weight of deltamethrin,
 b) from 5 to 15% by weight of wetting agent,
 c) from 10 to 30% by weight of dispersant,
 d) from 10 to 70% by weight of a solid inert substance,
 e) one or more acids in an amount sufficient to adjust the pH of the mixture to a value in the range from 1 to 7.

Deltamethrin is commercially available from Aventis CropScience SA, Lyon, France.

Suitable wetting agents are, for example, alkylnaphthalenesulfonate, such as Supragil WP® (Rhodia GmbH), N,N-dialkyltaurates, such as Arkopon T® (Clariant GmbH) or Geropon T-77® (Rhodia GmbH) or, preferably, a mixture of a sodium alkylnaphthalenesulfonate and the sodium salt of a sulfonated alkylcarboxylate, such as Morwet EFW® (Witco Corporation, Houston, USA).

The granules generally comprise from 5 to 15% by weight, particularly from 5 to 12% by weight, of wetting agent, which may be a mixture of a plurality of components.

Suitable for use as dispersants are, for example, modified sodium lignosulfonates, such as Borresperse Na®, Ufoxane 3A® and Ultrazine Na® (Borregard), Craft sodium lignosulfonates, such as Reax 88 B® (Westvaco) or naphthaline-formaldehyde condensates, such as Dispersing Agent SI® (Clariant GmbH), Morwet D425® (Witco Corporation) and Galoryl DT 201® (CFPI).

Preferred dispersants are sodium salts of alkylnaphthylsulfonic acid/formaldehyde condensates and sodium lignosulfonate which are commercially available, for example, under the names Morwet D425® (Witco Corp.) or Ufoxane 3A® (Borregard).

The formulation generally comprises from 2 to 30% by weight, preferably from 2 to 25% by weight, particularly preferably from 2 to 20% by weight of the dispersant which, if appropriate, may be a mixture of two or more components.

Suitable for use as the solid inert substance are, for example, substances such as talc, bentonites, silica, silicates, silica gels, synthetic silicates, attaclay, lime, loess, chalk, clay, dolomite, kieselguhr, diatonaceous earth, calcium sulfate, magnesium sulfate, magnesium oxide, ground plastics and resins, attapulgite, montmorillonite, vermiculite, mica, crushed or ground cereals, wood chips or wood meal, crushed or ground tree bark, crushed nutshells or cellulose.

The solid inert substance used is preferably kaolin, such as Argirec B24® from Blanc Mineraux de Paris, or China Clay from ECC International.

The formulation generally comprises from 10 to 80% by weight, preferably from 20 to 70% by weight, of the solid inert substance.

The acids used are preferably organic acids, in particular carboxylic acids, such as salicylic acid, particularly preferably di- and tricarboxylic acids, such as citric acid, succinic acid, tartaric acid or maleic acid, or mixtures of these.

The acid is added in an amount which is sufficient to adjust the pH of the formulation to a value in the range from 1 to 7, preferably from 2 to 6.

In addition to the components described, the formulations according to the invention may comprise further components customary in the formulation. Examples are antifoams, such as dialkylpolysiloxanes, for example Rhodorsil 416® (Rhodia, France), binders, such as polyvinyl alcohol, for example Mowiol 383® (Clariant, Germany), preservatives, such as benzoic acid or sorbic acid, or other customary adjuvants.

Granules according to the invention can be prepared by customary methods known to the person skilled in the art.

Thus, water-dispersible granules are prepared by the extrusion process, usually by mixing the active compound with the formulation auxiliaries and an inert material, subsequent dry grinding of this mixture (not required if the starting material particles are fine enough), moistening this powder with a suitable amount of water and subsequent compacting of the material in an extruder. Granules produced in this manner are dried and, if appropriate, comminuted or fractioned to give granules of a suitable size.

For granules according to the invention which are prepared by the preferred fluidized-bed process, an aqueous dispersion of active compound, formulation auxiliaries and inert material is prepared which generally contains 40–70% of dry material and which is generally ground wet. The use of a dispersion of active compound as starting material for granules is more economical than the use of an active compound powder such as an extrusion granulation, since wet grinding, compared to dry grinding, is safer from a technical point of view and easier to carry out, and thus also more cost-effective. This dispersion is preferably granulated in a countercurrent process by spraying it into a chamber through which heated air is passed in countercurrent. This results in the evaporation of water. The evaporated water is expelled from the chamber by the countercurrent air. The non-volatile components remain in the form of a powder which is fluidized by the air that is let in. On these powder particles, more of the sprayed-in dispersion is deposited, the water evaporates and as a result granules are formed which are characterized by a large particle surface, a round particle form and, compared to the compacted extrusion granules, a very light structure.

Such a process is likewise provided by the invention.

When using the granules prepared according to the invention, the relatively large surface of the granules, together with their light structure, results in better wetting with water and thus a more rapid dispersion in the spray liquor. The formulation powder which serves as initial charge can also, instead of being sprayed directly into the granulation chamber, be prepared by spray-drying. It is also possible for the formulation powder to be replaced by a dry-mixed mixture of the formulation components.

The formulations according to the invention are suitable for controlling pests in crop protection, and also, preferably, for the control of vectors and for the control of hygiene and stored-product pests living in storage areas, farms and gardens. Use for professional pest control by pest-control experts is preferred. The pests are generally animal pests, in particular arthropods, such as, for example, cockroaches. For use, the granules according to the invention are dispersed in water.

The present invention also provides the use of a formulation according to the invention for controlling pests, and also a method for controlling pests, such as cockroaches, which comprises applying a formulation according to the invention in the form of an aqueous dispersion onto the pests or the locations visited by them.

The content of the German patent application 100 480 06.3, the priority of which is claimed by the present application, and the appended abstract are hereby incorporated by reference.

The invention is illustrated by the examples below without being limited thereby.

For the preparation according to the fluidized-bed process, the formulation components were dispersed in water and ground wet. The dispersion of active compound was then sprayed into the granulation chamber in a countercurrent process. The resulting formulation powder was, by further spraying-on of dispersion, built up to give granules. To this end, a laboratory fluidized-bed granulator Büchi 710 from Büchi Laboratorium-Technik AG was used. Relatively large batches were prepared using an apparatus type S-3 from Aeromatic Fielder AG having a volume of about 20 kg.

The composition of the granules is identical to the dry material of the dispersion that is sprayed in.

EXAMPLE 1

|  | % by weight |
| --- | --- |
| Deltamethrin | 25 |
| Sodium salt of an alkylnaphthylsulfonic acid/ Formaldehyde condensate (Morwet D425 ®, Witco Corp.) | 16 |
| Mixture of a sodium alkylnaphthalenesulfonate and the sodium salt of a sulfonated alkylcarboxylate (Morwet EFW ®, Witco Corp.) | 8 |
| China Clay Grade D | 49 |
| Citric acid | 2 |

EXAMPLE 2

|  | % by weight |
| --- | --- |
| Deltamethrin | 25 |
| Sodium salt of lignosulfonate (Ufoxane 3A ®, Borregaard) | 8 |
| Mixture of a sodium alkylnaphthalenesulfonate and the sodium salt of a sulfonated alkylcarboxylate (Morwet EFW ®, Witco Corp.) | 10 |
| China Clay Grade D | 55 |
| Citric acid | 2 |

EXAMPLE 3

|  | % by weight |
| --- | --- |
| Deltamethrin | 25 |
| Sodium lignosulfonate (Borrespers Na ®, Borregaard) | 13 |
| Alkylnaphthalenesulfonate (Supragil WP ®, Rhodia GmbH) | 12 |
| China Clay Grade D | 47 |
| Tartaric acid | 3 |

EXAMPLE 4

|  | % by weight |
| --- | --- |
| Deltamethrin | 5 |
| Sodium salt of an alkylnaphthylsulfonic acid/ Formaldehyde condensate (Morwet D425 ®, Witco Corp.) | 16 |
| Mixture of a sodium alkylnaphthalenesulfonate and the sodium salt of a sulfonated alkylcarboxylate (Morwet EFW ®, Witco Corp.) | 8 |
| China Clay Grade D | 69 |
| Citric acid | 2 |

EXAMPLE 5

|  | % by weight |
| --- | --- |
| Deltamethrin | 25 |
| Naphthalenesulfonic acid/formaldehyde condensate (Galoryl DT 201 ®, CFPI Industries) | 20 |
| N,N-Dialkyltaurate (Arkopon T ®, Clariant GmbH) | 5 |
| China Clay Grade D | 47 |
| Succinic acid | 3 |

EXAMPLE 6

|  | % by weight |
| --- | --- |
| Deltamethrin | 50 |
| Sodium salt of an alkylnaphthylsulfonic acid/ formaldehyde condensate (Morwet D425 ®, Witco Corp.) | 16 |
| Mixture of a sodium alkylnaphthalenesulfonate and the sodium salt of a sulfonated alkylcarboxylate (Morwet EFW ®, Witco Corp.) | 8 |
| China Clay Grade D | 24 |
| Citric acid | 2 |

EXAMPLE 7

|  | % by weight |
| --- | --- |
| Deltamethrin | 25 |
| Kraft sodium lignosulfonate (Reax 88 B ®, Westvaco) | 15 |
| Mixture of a sodium alkylnaphthalenesulfonate and the sodium salt of a sulfonated alkylcarboxylate (Morwet EFW ®, Witco Corp.) | 10 |

-continued

| | % by weight |
|---|---|
| Kaolin (Argirec B24 ®) | 46 |
| Tartaric acid | 4 |

EXAMPLE 8

| | % by weight |
|---|---|
| Deltamethrin | 25 |
| Kraft sodium lignosulfonate (Reax 88 B ®, Westvaco) | 2 |
| Mixture of a sodium alkylnaphthalenesulfonate and the sodium salt of a sulfonated alkylcarboxylate (Morwet EFW ®, Witco Corp.) | 12 |
| China Clay Grade D | 59 |
| Citric acid | 2 |

EXAMPLE 9

The granules from Example 1 were diluted in water to give a 0.125% by weight strength dispersion. This dispersion was sprayed onto various surfaces such as cement flooring or plywood, at an application range of 6.25 mg of deltamethrin per $m^2$. The surfaces treated in this manner were put into storage and, after 1, 7 and 30 days, examined for their effectiveness against American cockroaches (*Periplaneta americana*). To this end, a number of cockroaches were placed onto the surface, and the mortality after 1 and 6 days was determined. For comparison, a commercial 2.5% by weight strength suspension concentrate (SC) formulation of deltamethrin was used.

The results were as follows: (dat=days after treatment of the surface)

| | % mortality | | | | | |
|---|---|---|---|---|---|---|
| Treatment | 1 dat (1 day later) | 1 dat (6 days later) | 7 dat (1 day later) | 7 dat (6 days later) | 30 dat (1 day later) | 30 dat (6 days later) |
| Example 1 on plywood | 27 | 53 | 87 | 100 | 53 | 60 |
| SC on plywood | 13 | 53 | 0 | 20 | 47 | 53 |
| Example 1 on concrete flooring | 100 | 100 | 100 | 100 | 100 | 100 |
| SC on concrete flooring | 20 | 27 | 27 | 13 | 0 | 0 |

It is surprising that the formulation according to the invention shows better results than the suspension concentrate.

EXAMPLE 10

The granules from Example 1 and 2 were diluted in water to give 0.125% by weight strength dispersion. These dispersions were sprayed onto ceramic, at an application rate of 6.25 mg of deltamethrin per $m^2$. The surfaces treated in this manner were put into storage and, after different storage times, examined for their effectiveness against American cockroaches (*Periplaneta americana*). The mortality of the cockroaches was determined after given periods of time. For comparison, a commercial 2.5% strength suspension concentrate (SC) formulation of deltamethrin was used.

The results were as follows:

| Treatment | % mortality 101 day old layer |
|---|---|
| Example 1 on ceramic | 100 |
| Example 2 on ceramic | 100 |
| SC on ceramic | 93 |

It can be seen that the formulations according to the invention give better results than the suspension concentrate.

What is claimed is:

1. Solvent-free, water dispersible granules, comprising:
   a) from 5 to 60% by weight of deltamethrin,
   b) from 5 to 15% by weight of at least one wetting agent,
   c) from 10 to 30% by weight of at least one dispersant,
   d) from 10 to 70% by weight of at least one solid inert substance, and
   e) one or more acids in an amount sufficient to adjust, when the granules are dispersed in water, the pH of the resulting aqueous dispersion to a value in the range from 1 to 7.

2. A method for controlling arthropods, where granules as claimed in claim 1 are converted into an aqueous dispersion and this dispersion is applied in an effective amount onto the arthropods or locations visited by them.

3. A process for preparing solvent-free, water dispersible granules, which comprise:
   a) from 5 to 60% by weight of deltamethrin,
   b) from 5 to 15% by weight of at least one wetting agent,
   c) from 10 to 30% by weight of at least one dispersant,
   d) from 10 to 70% by weight of at least one solid inert substance, and
   e) one or more acids in an amount sufficient to adjust, when the granules are dispersed in water, to adjust the pH of the resulting aqueous dispersion to a value in the range of 1 to 7, said process comprising:
   1) preparing an aqueous dispersion comprising
      a) from 5 to 60% by weight of deltamethrin,
      b) from 5 to 15% by weight of at least one wetting agent,
      c) from 10 to 30% by weight of at least one dispersant,
      d) from 10 to 70% by weight of at least one solid inert substance, and
      e) one or more acids in an amount sufficient to adjust, when the granules are dispersed in water to adjust the pH of the resulting aqueous solution to a value in the range of 1 to 7, and wet grinding the aqueous dispersion, and
   2) continuously spraying the aqueous dispersion prepared in step 1) into a chamber through which heated air is passed in countercurrent.

* * * * *